(12) United States Patent
DellaPenna et al.

(10) Patent No.: US 6,642,434 B1
(45) Date of Patent: Nov. 4, 2003

(54) TRANSGENIC PLANTS WITH γ-TOCOPHEROL METHYLTRANSFERASE

(75) Inventors: Dean DellaPenna, Reno, NV (US); David K. Shintani, Reno, NV (US)

(73) Assignee: University of Community College System of Nevada, Reno, NV (US)

( * ) Notice: Subject to any disclaimer, the term of this patent is extended or adjusted under 35 U.S.C. 154(b) by 0 days.

(21) Appl. No.: 09/118,637

(22) Filed: Jul. 17, 1998

Related U.S. Application Data

(60) Provisional application No. 60/053,819, filed on Jul. 25, 1997, and provisional application No. 60/072,497, filed on Jan. 26, 1998.

(51) Int. Cl.[7] ............... C12N 15/29; C12N 5/04; C12N 15/82; C12P 21/06; C07H 21/04

(52) U.S. Cl. ............... 800/278; 435/69.1; 435/70.1; 435/410; 435/419; 536/23.1; 536/23.6; 536/23.2; 800/295; 800/306; 800/298

(58) Field of Search ............... 435/69.1, 70.1, 435/410, 419; 536/23.1, 23.6, 23.2; 800/295, 278, 306, 298

(56) References Cited

PUBLICATIONS

Alscher et al. Anitoxidants in Higher Plants. CRC press. 1993.*
Smith at al. Nature. 1988. Vol. 334: 724–726, 1988.*
Kaneko et al. 1995. DNA Research. 2: 153–166 (Accession number enclosed: BAA10562), 1995.*
Fillatti et al. Biotechnology. 1987. Vol. 5: 726–730, 1987.*
d'Harlingue, Alain and Bilal Camara, "Plastid Enzymes of Terpenoid Biosynthesis; Purification and Characterization of γ–Tocopherol Methyltransferase from *Capsicum* Chromoplasts", *J. Biol. Chem.* 260(28): 15200–15203 (1985).

Hess, John L., "Vitamin E, α–Tocopherol" in *Antioxidants in Highter Plants* edited by Alscher, Ruth G. and John L. Hess, CRC Press, Inc. pp. 111–134 (1993).

Ishiko et al., "Some Properties of γ–Tocopherol Methyltransferase Solubilized from Spinach Chloroplasts", *Phytochemistry* 31(5):1499–1500 (1992).

Mullineaux, P.M. and G.P. Creissen, "Opportunities for the Genetic Manipulation of Antioxidants in Plant Foods", *Biochemical Society Transactions* 24(3): 829–835 (1996).

Shiegeoka et al., "Isolation and Properties of γ–Tocopherol Methyltransferase in *Euglena gracilis*", *Biochimica et Biophysica Acta* 1128:220–226 (1992).

* cited by examiner

*Primary Examiner*—Lynette R. F. Smith
*Assistant Examiner*—Ousama Zaghmout
(74) *Attorney, Agent, or Firm*—Quarles & Brady LLP

(57) ABSTRACT

Disclosed is are gene sequences encoding γ-tocopherol methyltransferases from photosynthetic organisms. The enzyme γ-tocopherol methyltransferase catalyzes the methylation of γ-tocopherol to yield α-tocopherol, the most bioactive species of tocopherol. γ-tocopherol methyltransferase is believed to be involved in regulating the relative amounts of the various tocopherols present in photosynthetic organisms. By introducing a genetic construct having a γ-tocopherol methyltransferase coding sequence placed under the control of a plant promoter into a plant, transgenic plants can be made having altered γ-tocopherol methyltransferase expression, to effect dramatic changes in the tocopherol profile of the plant. Transgenic plants can be made that have α-tocopherol as the predominant tocopherol in their seeds and oils.

12 Claims, 1 Drawing Sheet

FIG 1

|  | | |
|---|---|---|
| Synecco.gTMT | 1 | - - - - - - - - - - - - - - - - - - - - - - - - - - - - - - - - - - - - - - M V Y H V R P K H A L F L A F |
| A.t.gTMT | 1 | M K A T L A A P S S L T S L P Y R T N S S F G S K S S L L F R S P S S S S V S M |
| Synecco.gTMT | 16 | Y C Y F S L L T M A S A T I A S A D L Y E K I K N F Y D D S S G L W E D V W G E H |
| A.t.gTMT | 42 | T T T R G N V A V A A A T S T E A L R K G I A E F Y N E T S G L W E E I W G D H |
| Synecco.gTMT | 57 | M H H G Y Y G P H G T Y R I D - - R R Q A Q D L I K E L L A W A V P Q N S - - |
| A.t.gTMT | 83 | M H G F Y D P D S S V Q L S D S G H K E A Q I R M E E S L R F A G V T D E E E |
| Synecco.gTMT | 93 | - A K P R K I L D L G C G I G G S S L Y L A Q Q H Q A E V M G A S L S P V Q V E R |
| A.t.gTMT | 124 | E K K I K K V V D V G C G I G G S S R Y L A S K F G A E C I G I T L S P V Q A K R |
| Synecco.gTMT | 133 | A G E R A R A L G L G S T C Q F Q V A N A L D L P F A S D S F D W V W S L E S G E |
| A.t.gTMT | 165 | A N D L A A A Q S L S H K A S F Q V A D A L D Q P F E D G K F D L V W S M E S G E |
| Synecco.gTMT | 174 | - A K P R V L K P G R L I L A T W C H R P I D P G N G P L T A |
| A.t.gTMT | 206 | E A W R V L K P G G R L I L A T W C H R P I D P G N G P L T A |
| Synecco.gTMT | 215 | H M P N K A Q F L Q E A W R V L K P G R L I L A T W C H R P I D P G N G P L T A |
| A.t.gTMT | 247 | H M P D K A K F V K E L V R V A A P G G R I T I V T W C H R N L S A G E E A L Q P |
| Synecco.gTMT | 256 | D E R R H L Q A I Y D V Y C L P Y V V S L P D Y E A I A R E C G F G E F K T A D W |
| A.t.gTMT | 288 | W E Q N I L D K I C K T F Y L P A W C S T D D Y V N L L Q S H S L Q D I K C A D W |
| Synecco.gTMT | 297 | S V A V A P F W D R V I E S A F D P R V L W A L G Q A G P K I T N A L C L R L M |
| A.t.gTMT | 329 | S E N V A P F W P A V I R T A L T W K G L V S L R S G M K S I K G A L T M P L M |
| Synecco.gTMT |  | K W G Y E R G L V R F G L L T G I K P L V |
| A.t.gTMT |  | I E G Y K K G V I K F G I T C Q K P L - |

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..954

(xi) SEQUENCE DESCRIPTION: SEQ ID NO:1:

```
ATG GTT TAC CAT GTT AGG CCT AAG CAC GCC CTG TTC TTA GCA TTC TAT      48
Met Val Tyr His Val Arg Pro Lys His Ala Leu Phe Leu Ala Phe Tyr
 1               5                  10                  15

TGT TAT TTC TCT TTG CTT ACC ATG GCC AGC GCC ACC ATT GCC AGT GCA      96
Cys Tyr Phe Ser Leu Leu Thr Met Ala Ser Ala Thr Ile Ala Ser Ala
```

```
                 20                  25                  30
GAC CTC TAC GAA AAA ATT AAA AAT TTC TAC GAC GAC TCC AGC GGT CTC         144
Asp Leu Tyr Glu Lys Ile Lys Asn Phe Tyr Asp Asp Ser Ser Gly Leu
         35                  40                  45

TGG GAA GAC GTT TGG GGT GAG CAT ATG CAC CAC GGC TAC TAC GGT CCC         192
Trp Glu Asp Val Trp Gly Glu His Met His His Gly Tyr Tyr Gly Pro
     50                  55                  60

CAC GGC ACC TAT CGG ATC GAT CGC CGC CAG GCT CAA ATT GAT CTG ATC         240
His Gly Thr Tyr Arg Ile Asp Arg Arg Gln Ala Gln Ile Asp Leu Ile
 65                  70                  75                  80

AAA GAA CTA TTG GCC TGG GCA GTG CCC CAA AAT AGC GCC AAA CCA CGA         288
Lys Glu Leu Leu Ala Trp Ala Val Pro Gln Asn Ser Ala Lys Pro Arg
                 85                  90                  95

AAA ATT CTC GAT TTA GGC TGT GGC ATT GGC GGC AGT AGT TTG TAC TTG         336
Lys Ile Leu Asp Leu Gly Cys Gly Ile Gly Gly Ser Ser Leu Tyr Leu
             100                 105                 110

GCC CAG CAA CAC CAA GCA GAA GTG ATG GGG GCT AGT CTT TCC CCA GTG         384
Ala Gln Gln His Gln Ala Glu Val Met Gly Ala Ser Leu Ser Pro Val
         115                 120                 125

CAG GTG GAA CGG GCG GGG GAA AGG GCC AGG GCC CTG GGG TTG GGC TCA         432
Gln Val Glu Arg Ala Gly Glu Arg Ala Arg Ala Leu Gly Leu Gly Ser
     130                 135                 140

ACC TGC CAG TTT CAG GTG GCC AAT GCC TTG GAT TTG CCC TTT GCT TCC         480
Thr Cys Gln Phe Gln Val Ala Asn Ala Leu Asp Leu Pro Phe Ala Ser
145                 150                 155                 160

GAT TCC TTT GAC TGG GTT TGG TCG TTG GAA AGT GGG GAG CAC ATG CCC         528
Asp Ser Phe Asp Trp Val Trp Ser Leu Glu Ser Gly Glu His Met Pro
                 165                 170                 175

AAC AAA GCT CAG TTT TTA CAA GAA GCT TGG CGG GTA CTT AAA CCA GGT         576
Asn Lys Ala Gln Phe Leu Gln Glu Ala Trp Arg Val Leu Lys Pro Gly
             180                 185                 190

GGC CGT CTG ATT TTA GCG ACC TGG TGT CAT CGT CCC ATT GAT CCC GGC         624
Gly Arg Leu Ile Leu Ala Thr Trp Cys His Arg Pro Ile Asp Pro Gly
         195                 200                 205

AAT GGC CCC CTG ACT GCC GAT GAA CGT CGC CAT CTC CAA GCC ATC TAT         672
Asn Gly Pro Leu Thr Ala Asp Glu Arg Arg His Leu Gln Ala Ile Tyr
     210                 215                 220

GAC GTT TAC TGT TTG CCC TAT GTG GTT TCC CTG CCG GAC TAC GAG GCG         720
Asp Val Tyr Cys Leu Pro Tyr Val Val Ser Leu Pro Asp Tyr Glu Ala
225                 230                 235                 240

ATC GCC AGG GAA TGT GGG TTT GGG GAA ATT AAG ACT GCC GAT TGG TCA         768
Ile Ala Arg Glu Cys Gly Phe Gly Glu Ile Lys Thr Ala Asp Trp Ser
                 245                 250                 255

GTG GCG GTG GCA CCT TTT TGG GAC CGG GTG ATT GAG TCT GCG TTC GAT         816
Val Ala Val Ala Pro Phe Trp Asp Arg Val Ile Glu Ser Ala Phe Asp
             260                 265                 270

CCC CGG GTG TTG TGG GCC TTG GGG CAA GCG GGG CCA AAA ATT ATC AAT         864
Pro Arg Val Leu Trp Ala Leu Gly Gln Ala Gly Pro Lys Ile Ile Asn
         275                 280                 285

GCC GCC CTG TGT TTA CGA TTA ATG AAA TGG GGC TAT GAA CGG GGA TTA         912
Ala Ala Leu Cys Leu Arg Leu Met Lys Trp Gly Tyr Glu Arg Gly Leu
     290                 295                 300

GTG CGT TTT GGC TTA TTA ACG GGG ATA AAG CCT TTA GTT TGA                 954
Val Arg Phe Gly Leu Leu Thr Gly Ile Lys Pro Leu Val *
305                 310                 315

(2) INFORMATION FOR SEQ ID NO:2:

(i) SEQUENCE CHARACTERISTICS:
        (A) LENGTH:  317 amino acids
```

(B) TYPE: amino acid
        (D) TOPOLOGY: linear (ii) MOLECULE TYPE: protein (xi) SEQUENCE DESCRIPTION: SEQ ID NO:2:

Met Val Tyr His Val Arg Pro Lys His Ala Leu Phe Leu Ala Phe Tyr
 1               5                  10                  15

Cys Tyr Phe Ser Leu Leu Thr Met Ala Ser Ala Thr Ile Ala Ser Ala
                20                  25                  30

Asp Leu Tyr Glu Lys Ile Lys Asn Phe Tyr Asp Asp Ser Ser Gly Leu
            35                  40                  45

Trp Glu Asp Val Trp Gly Glu His Met His Gly Tyr Tyr Gly Pro
    50                  55                  60

His Gly Thr Tyr Arg Ile Asp Arg Arg Gln Ala Gln Ile Asp Leu Ile
 65                  70                  75                  80

Lys Glu Leu Leu Ala Trp Ala Val Pro Gln Asn Ser Ala Lys Pro Arg
                85                  90                  95

Lys Ile Leu Asp Leu Gly Cys Gly Ile Gly Gly Ser Ser Leu Tyr Leu
            100                 105                 110

Ala Gln Gln His Gln Ala Glu Val Met Gly Ala Ser Leu Ser Pro Val
        115                 120                 125

Gln Val Glu Arg Ala Gly Glu Arg Ala Arg Ala Leu Gly Leu Gly Ser
    130                 135                 140

Thr Cys Gln Phe Gln Val Ala Asn Ala Leu Asp Leu Pro Phe Ala Ser
145                 150                 155                 160

Asp Ser Phe Asp Trp Val Trp Ser Leu Glu Ser Gly Glu His Met Pro
                165                 170                 175

Asn Lys Ala Gln Phe Leu Gln Glu Ala Trp Arg Val Leu Lys Pro Gly
            180                 185                 190

Gly Arg Leu Ile Leu Ala Thr Trp Cys His Arg Pro Ile Asp Pro Gly
        195                 200                 205

Asn Gly Pro Leu Thr Ala Asp Glu Arg Arg His Leu Gln Ala Ile Tyr
    210                 215                 220

Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
            260                 265                 270

Pro Arg Val Leu Trp Ala Leu Gly Gln Ala Gly Pro Lys Ile Ile Asn
        275                 280                 285

Ala Ala Leu Cys Leu Arg Leu Met Lys Trp Gly Tyr Glu Arg Gly Leu
    290                 295                 300

Val Arg Phe Gly Leu Leu Thr Gly Ile Lys Pro Leu Val
305                 310                 315

(2) INFORMATION FOR SEQ ID NO:3:

(i) SEQUENCE CHARACTERISTICS:
        (A) LENGTH: 1790 base pairs
        (B) TYPE: nucleic acid
        (C) STRANDEDNESS: double
        (D) TOPOLOGY: linear (ii) MOLECULE TYPE: cDNA (ix) FEATURE:

(A) NAME/KEY: CDS
(B) LOCATION: 207..1253

(xi) SEQUENCE DESCRIPTION: SEQ ID NO:3:

| | |
|---|---|
| GCTCGCATGT TGTGTGGAAT TGTGAGCGGA TAACAATTTC ACACAGGAAA CAGCTATGAC | 60 |
| CATGATTACG CCAAGCTCTA ATACGACTCA CTATAGGGAA AGCTGGTACG CCTGCAGGTA | 120 |
| CCGGTCCGGA ATTCCCGGGT CGACCCACGC GTCCGCAAAT AATCCCTGAC TTCGTCACGT | 180 |

```
TTCTTTGTAT CTCCAACGTC CAATAA ATG AAA GCA ACT CTA GCA GCA CCC TCT    233
                              Met Lys Ala Thr Leu Ala Ala Pro Ser
                              320             325

TCT CTC ACA AGC CTC CCT TAT CGA ACC AAC TCT TCT TTC GGC TCA AAG    281
Ser Leu Thr Ser Leu Pro Tyr Arg Thr Asn Ser Ser Phe Gly Ser Lys
        330                 335                 340

TCA TCG CTT CTC TTT CGG TCT CCA TCC TCC TCC TCC TCA GTC TCT ATG    329
Ser Ser Leu Leu Phe Arg Ser Pro Ser Ser Ser Ser Ser Val Ser Met
345                 350                 355

ACG ACA ACG CGT GGA AAC GTG GCT GTG GCG GCT GCT GCT ACA TCC ACT    377
Thr Thr Thr Arg Gly Asn Val Ala Val Ala Ala Ala Ala Thr Ser Thr
360                 365                 370                 375

GAG GCG CTA AGA AAA GGA ATA GCG GAG TTC TAC AAT GAA ACT TCG GGT    425
Glu Ala Leu Arg Lys Gly Ile Ala Glu Phe Tyr Asn Glu Thr Ser Gly
                380                 385                 390

TTG TGG GAA GAG ATT TGG GGA GAT CAT ATG CAT CAT GGC TTT TAT GAC    473
Leu Trp Glu Glu Ile Trp Gly Asp His Met His His Gly Phe Tyr Asp
            395                 400                 405

CCT GAT TCT TCT GTT CAA CTT TCT GAT TCT GGT CAC AAG GAA GCT CAG    521
Pro Asp Ser Ser Val Gln Leu Ser Asp Ser Gly His Lys Glu Ala Gln
        410                 415                 420

ATC CGT ATG ATT GAA GAG TCT CTC CGT TTC GCC GGT GTT ACT GAT GAA    569
Ile Arg Met Ile Glu Glu Ser Leu Arg Phe Ala Gly Val Thr Asp Glu
425                 430                 435

GAG GAG GAG AAA AAG ATA AAG AAA GTA GTG GAT GTT GGG TGT GGG ATT    617
Glu Glu Glu Lys Lys Ile Lys Lys Val Val Asp Val Gly Cys Gly Ile
440                 445                 450                 455

GGA GGA AGC TCA AGA TAT CTT GCC TCT AAA TTT GGA GCT GAA TGC ATT    665
Gly Gly Ser Ser Arg Tyr Leu Ala Ser Lys Phe Gly Ala Glu Cys Ile
                460                 465                 470

GGC ATT ACT CTC AGC CCT GTT CAG GCC AAG AGA GCC AAT GAT CTC GCG    713
Gly Ile Thr Leu Ser Pro Val Gln Ala Lys Arg Ala Asn Asp Leu Ala
            475                 480                 485

GCT GCT CAA TCA CTC TCT CAT AAG GCT TCC TTC CAA GTT GCG GAT GCG    761
Ala Ala Gln Ser Leu Ser His Lys Ala Ser Phe Gln Val Ala Asp Ala
        490                 495                 500

TTG GAT CAG CCA TTC GAA GAT GGA AAA TTC GAT CTA GTG TGG TCG ATG    809
Leu Asp Gln Pro Phe Glu Asp Gly Lys Phe Asp Leu Val Trp Ser Met
505                 510                 515

GAG AGT GGT GAG CAT ATG CCT GAC AAG GCC AAG TTT GTA AAA GAG TTG    857
Glu Ser Gly Glu His Met Pro Asp Lys Ala Lys Phe Val Lys Glu Leu
520                 525                 530                 535

GTA CGT GTG GCG GCT CCA GGA GGT AGG ATA ATA ATA GTG ACA TGG TGC    905
Val Arg Val Ala Ala Pro Gly Gly Arg Ile Ile Ile Val Thr Trp Cys
                540                 545                 550

CAT AGA AAT CTA TCT GCG GGG GAG GAA GCT TTG CAG CCG TGG GAG CAA    953
His Arg Asn Leu Ser Ala Gly Glu Glu Ala Leu Gln Pro Trp Glu Gln
            555                 560                 565

AAC ATC TTG GAC AAA ATC TGT AAG ACG TTC TAT CTC CCG GCT TGG TGC    1001
Asn Ile Leu Asp Lys Ile Cys Lys Thr Phe Tyr Leu Pro Ala Trp Cys
        570                 575                 580
```

-continued

```
TCC ACC GAT GAT TAT GTC AAC TTG CTT CAA TCC CAT TCT CTC CAG GAT      1049
Ser Thr Asp Asp Tyr Val Asn Leu Leu Gln Ser His Ser Leu Gln Asp
    585                 590                 595

ATT AAG TGT GCG GAT TGG TCA GAG AAC GTA GCT CCT TTC TGG CCT GCG      1097
Ile Lys Cys Ala Asp Trp Ser Glu Asn Val Ala Pro Phe Trp Pro Ala
600                 605                 610                 615

GTT ATA CGG ACT GCA TTA ACA TGG AAG GGC CTT GTG TCT CTG CTT CGT      1145
Val Ile Arg Thr Ala Leu Thr Trp Lys Gly Leu Val Ser Leu Leu Arg
                620                 625                 630

AGT GGT ATG AAA AGT ATT AAA GGA GCA TTG ACA ATG CCA TTG ATG ATT      1193
Ser Gly Met Lys Ser Ile Lys Gly Ala Leu Thr Met Pro Leu Met Ile
            635                 640                 645

GAA GGT TAC AAG AAA GGT GTC ATT AAG TTT GGT ATC ATC ACT TGC CAG      1241
Glu Gly Tyr Lys Lys Gly Val Ile Lys Phe Gly Ile Ile Thr Cys Gln
        650                 655                 660

AAG CCA CTC TAA GTCTAAAGCT ATACTAGGAG ATTCAATAAG ACTATAAGAG          1293
Lys Pro Leu *
    665

TAGTGTCTCA TGTGAAAGCA TGAAATTCCT TAAAAACGTC AATGTTAAGC CTATGCTTCG   1353

TTATTTGTTT TAGATAAGTA TCATTTCACT CTTGTCTAAG GTAGTTTCTA TAAACAATAA   1413

ATACCATGAA TTAGCTCATG TTATCTGGTA AATTCTCGGA AGTGATTGTC ATGGATTAAC   1473

TCAAAAAAAA AAAAAAAAAA AGGGCGGCCG CTCTAGAGGA TCCAAGCTTA CGTACGCGTG   1533

CATGCGACGT CATAAGTCTA TCATACCGTC GACCTCGAGG GGGGCCCTAA ATTCAATTCA   1593

CTGGCCGTCG TTTTACAACG TCGTGACTGG GAAAACCCTG GCGTTACCCA ACTTAATCGC   1653

CTTGCAGCAC ATCCCCCTTT CGCCAGCTGG CGTAATAGCG AAGAGGCCCG CACCGATCGC   1713

CCTTCCCAAC AGTTGCGCAG CCTGAATGGC GAATGGGACG CGCCCTGTAG CGGCGCATTA   1773

AGCGCGGCGG GTGTGGT                                                  1790
```

(2) INFORMATION FOR SEQ ID NO:4:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
            20                  25                  30

Pro Ser Ser Ser Ser Val Ser Met Thr Thr Thr Arg Gly Asn Val
        35                  40                  45

Ala Val Ala Ala Ala Thr Ser Thr Glu Ala Leu Arg Lys Gly Ile
    50                  55                  60

Ala Glu Phe Tyr Asn Glu Thr Ser Gly Leu Trp Glu Glu Ile Trp Gly
65                  70                  75                  80

Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
```

```
                130             135             140
Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Gln Ser Leu Ser His
                165                 170                 175

Lys Ala Ser Phe Gln Val Ala Asp Ala Leu Asp Gln Pro Phe Glu Asp
                180                 185                 190

Gly Lys Phe Asp Leu Val Trp Ser Met Glu Ser Gly Glu His Met Pro
                195                 200                 205

Asp Lys Ala Lys Phe Val Lys Glu Leu Val Arg Val Ala Ala Pro Gly
210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
                260                 265                 270

Leu Leu Gln Ser His Ser Leu Gln Asp Ile Lys Cys Ala Asp Trp Ser
                275                 280                 285

Glu Asn Val Ala Pro Phe Trp Pro Ala Val Ile Arg Thr Ala Leu Thr
290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
                340                 345
```

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

ACGGATCCAA AAATGCCTAT GGTTCATCAT CGGGG                35

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:6:

GGGGATCCTG TGGACTTCAA ACTAAAGGCT TTATC                35

(2) INFORMATION FOR SEQ ID NO:7:

(i) SEQUENCE CHARACTERISTICS:
        (A) LENGTH: 24 base pairs
        (B) TYPE: nucleic acid

```
            (C) STRANDEDNESS: single
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:7:

CCTCATGATT TACCATGTTA GGCC                                          24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:8:

AGATCTCAAA CTAAAGGCTT TATC                                          24

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:9:

CCATGCTGTG GCGGCTGCTG CTAC                                          24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:10:

GTCGACGCAT GCACGCGTAC GTAA                                          24
```

TRANSGENIC PLANTS WITH γ-TOCOPHEROL METHYLTRANSFERASE

CROSS-REFERENCE TO RELATED APPLICATIONS

This application claims priority to U.S. Provisional Application Ser. No. 60/053,819 filed Jul. 25, 1997 and U.S. Provisional Application Ser. No. 60/072,497 filed Jan. 26, 1998.

STATEMENT REGARDING FEDERALLY SPONSORED RESEARCH OR DEVELOPMENT

Not applicable.

BACKGROUND OF THE INVENTION

Vitamin E is an essential component of mammalian diets. Epidemiological evidence indicates that Vitamin E supplementation results in decreased risk for cardiovascular disease and cancer, aids in immune function, and generally prevents or slows a number of degenerative disease processes in humans (Traber and Sies, Annu. Rev. Nutr. 16:321–347, 1996). Vitamin E functions in stabilizing the lipid bilayer of biological membranes (Skrypin and Kagan, Biochim. Biophys. Acta 815:209 1995; Kagan, N.Y. Acad. Sci. p 121, 1989; Gomez-Fernandez et al., Ann. N.Y. Acad. Sci. p 109, 1989), reducing polyunsaturated fatty acid (PUFA) free radicals generated by lipid oxidation (Fukuzawa et al., Lipids 17: 511–513, 1982), and quenching singlet oxygen species (Fryer, Plant Cell Environ. 15(4):381–392, 1992).

Vitamin E, or α-tocopherol, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "Vitamin E" in the popular press, Vitamin E is properly defined chemically solely as α-tocopherol. Of the various tocopherols present in foodstuff, α-tocopherol is the most significant for human health both because it is the most bioactive of the tocopherols and also because it is the tocopherol most readily absorbed and retained by the body (Traber and Sies, Annu. Rev. Nutr. 16:321–347, 1996). The in vivo antioxidant activity of α-tocopherol is higher than the antioxidant activities of β, γ, and δ-tocopherol (Kamal-Eldin and Appelqzvist Lipids 31:671–701, 1996).

Only plants and certain other photosynthetic organisms, including cyanobacteria, synthesize tocopherols. Therefore, dietary tocopherols are obtained almost exclusively from plants. Plant tissues vary considerably in total tocopherol content and tocopherol composition. The predominant tocopherol in green, photosynthetic plant tissues often is α-tocopherol. Leaf tissue can contain from 10–50 μg total tocopherols/gram fresh weight.

Non-green plant tissues and organs exhibit a wider range of both total tocopherol levels and tocopherol compositions. In general, most of the major food staple corps (e.g., rice, corn, wheat, potato) produce low to extremely low levels of total tocopherols, of which only a small percentage is α-tocopherol (Hess, Vitamin E, α-tocopherol, In Antioxidants in Higher Plants, R. Alscher and J. Hess, Eds. 1993, CRC Press, Boca Raton. pp 111–134). Oil seed crops generally contain much higher levels of total tocopherols; however, α-tocopherol is present only as a minor component and β, γ, and δ-tocopherols and tocotrienols predominate (Taylor and Barnes, Chemy Ind., October:722–726, 1981).

Daily dietary intake of 15–30 mg of vitamin E is recommended to obtain optimal plasma α-tocopherol levels. It is quite difficult to achieve this level of vitamin E intake from the average American diet. For example, one could obtain the recommended daily dose of Vitamin E by daily consumption of over 750 grams of spinach leaves (in which α-tocopherol comprises 60% of total tocopherols) or 200–400 grams of soybean oil.

One alternative to relying on diet alone to obtain the recommended levels of vitamin E is to take a vitamin E supplement. However, most vitamin E supplements are synthetic vitamin E having six stereoisomers, whereas natural vitamin E vitamin is a single isomer. Furthermore, supplements tend to be relatively expensive, and the general population is disinclined to take vitamin supplements on a regular basis.

Although tocopherol function in plants has been less extensively studied than tocopherol function in mammalian systems, it is likely that the analogous functions performed by tocopherols in animals also occur in plants. In general, plant tocopherol levels have been found to increase with increases in various stresses, especially oxidative stress. Increased α-tocopherol levels in crops are associated with enhanced stability and extended shelf life of fresh and processed plant products (Peterson, Cereal-Chem 72(1) :21–24, 1995; Ball, Fat-soluble vitamin assays in food analysis. A comprehensive review. London: Elsevier Science Publishers LTD, 1988).

Vitamin E supplementation of swine, beef, and poultry feeds has been shown to significantly increase meat quality and extend the shelf life of post-processed meat products by retarding post-processing lipid oxidation, which contributes to the formation of undesirable flavor components (Ball, supra 1988; Sante and Lacourt, J. Sci. Food Agric. 65(4) :503–507, 1994; Buckley et al., J. of Animal Science 73:3122–3130, 1995).

What would be useful for the art is a method to increase the ratio of α-tocopherol to γ-tocopherol in seeds, oils, and leaves from crop and forage plants, or a method for producing natural vitamin E in nonphotosynthetic bacteria or fungi using a large scale fermentation process. Increasing α-tocopherol levels in crop plants would increase the amount of α-tocopherol obtained in the human diet, and would enhance the stability and shelf life of plants and plant products. The meat industry would benefit from the development of forage plants having increased levels of vitamin E.

BRIEF SUMMARY OF THE INVENTION

The present invention is based on an isolated DNA fragment including a coding sequence for a γ-tocopherol methyltransferase.

The invention is also a heterologous genetic construct comprising a γ-tocopherol methyltransferase coding sequence operably connected to a plant, bacterial, or fungal promoter not natively associated with the γ-tocopherol methyltransferase coding sequence.

Another aspect of the present invention is a method of altering the tocopherol profile of a plant comprising the steps of: (a) providing a heterologous genetic construct comprising a γ-tocopherol methyltransferase coding sequence operably connected to a plant promoter not natively associated with the coding sequence; and (b) introducing the construct into the genome of a plant.

The present invention is also directed toward transgenic plants which have an altered ratio of α-tocopherol to γ-tocopherol, thus increasing the nutritive value of the plants and products therefrom for human and animals.

In another embodiment, the invention is a plant comprising in its genome a heterologous genetic construct comprising a γ-tocopherol methyltransferase coding sequence operably connected to a promoter that is functional in plants.

It is an object of the present invention to provide a genetic construct comprising a coding sequence for a γ-tocopherol methyltransferase operably connected to a plant promoter not natively associated with the coding sequence which when expressed in a plant comprising the construct in its genome results in an alteration in the ratio of α-tocopherol: γ-tocopherol in the plant, relative to an untransformed wild-type plant.

It is an object of this invention to provide a plant having an altered α-tocopherol: γ-tocopherol ratio.

Other objects, features, and advantages of the invention will become apparent upon review of the specification and claims.

BRIEF DESCRIPTION OF THE SEVERAL VIEWS OF THE DRAWINGS

FIG. 1 shows the alignment of amino acid sequences of γ-tocopherol methyl-transferases from *Arabidopsis thaliana* and Synechocystis. Inverted triangles denote putative cleavage sites of N-terminal targeting domains; the closed circle denotes the position of an in-frame NcoI site in the leader peptide of SLR0089.

DETAILED DESCRIPTION OF THE INVENTION

The present invention is, in part, directed to a plant comprising in its genome a genetic construct comprising a γ-tocopherol methyltransferase coding sequence operably connected to a plant promoter not natively associated with the coding sequence. Such transgenic plants exhibit an altered ratio relative to the wild type plants of the same species. In fact, seed and seed oil of a plant not normally containing α-tocopherol can be altered so that the most abundant tocopherol is α-tocopherol. Alternatively, the relative percentage of γ-tocopherol present in plant tissue may be increased by reducing the activity of γ-tocopherol methyltransferase in the plant, which could be accomplished by expression of a γ-tocopherol methyltransferase coding sequence in the antisense orientation. The development of plants with increased γ-tocopherol may be useful in certain industries.

Tocopherols and plastoquinones, the most abundant quinones in plant plastids, are synthesized by a common pathway (Hess, *Antioxidants in Higher Plants*, CRC Press: Boca Raton p 140–152, 1993; Soll, *Plant Cell Membranes*, Academic Press: San Diego p 383–392, 1987). The synthesis of tocopherols involves four steps catalyzed by at least six enzymatic activities. A branchpoint in the common pathway occurs upon phytylation or prenylation of the precursor homogentisic acid to form either 2-methyl-6-phytylplastoquinol or 2-methyl-6-solanylplastoquinol, intermediates in tocopherol and plastoquinone biosynthesis, respectively.

The intermediate 2-methyl-6-phytylplastoquinol is the common precursor to the biosynthesis of all tocopherols. In spinach leaves, the intermediate undergoes ring methylation to yield 2,3-dimethyl-6-phytylplastoquinol, which is cyclized to form γ-tocopherol. A second ring methylation at position 5 yields α-tocopherol (Soll and Schultz, *Phytochemistry* 19(2):215–218, 1980). The second ring methylation is catalyzed by γ-tocopherol methyltransferase, a distinct enzymatic activity from the methyltransferase that catalyzes the methylation at position 7, and the only enzyme of the pathway that has been purified from plants (d'Harlingue and Camara, *J. Biol. Chem.* 260(68): 15200–15203, 1985; Ishiko et al., *Phytochemistry* 31(5):1499–1500, 1992).

The methylation enzymes are involved in regulating the final composition of the tocopherol pool. Data obtained in studies of sunflower mutants suggest that the enzymes involved in methylation have a high degree of influence over relative tocopherol amounts but do not affect the overall regulation of total tocopherol content (Demurin, *Helia* 16:59–62, 1993). Normally, seed tocopherol composition in cultivated sunflower (*Helianthus annuus* L.) is primarily α-tocopherol (i.e., 95–100% of the total tocopherol pool) (Skoric et al., Proceedings of the 14th International Sunflower Conference. 1996. Beijing/Shenyang, China). However, two mutant sunflower lines were identified with tocopherol compositions of 95% γ-tocopherol/5% α-tocopherol and 50% β-tocopherol/50% α-tocopherol. Although these presumed tocopherol methylation mutants were found to have dramatically different tocopherol profiles in seed, total tocopherol levels were not significantly different than those of wild type sunflower (Demurin, supra 1993). Based on these results, we hypothesized that it should be possible to alter the tocopherol profile of many plant species by manipulating γ-tocopherol methyltransferase expression without affecting the total tocopherol pool size.

The enzyme γ-tocopherol methyltransferase catalyzes the methylation of γ-tocopherol to form α-tocopherol, the final step in α-tocopherol biosynthesis. Overexpression of a γ-tocopherol methyltransferase gene in a plant enhanced the conversion of γ-tocopherol to α-tocopherol in any tissue containing γ-tocopherol, thereby increasing the α-tocopherol: γ-tocopherol ratio. In fact, seed and oil in which little or no α-tocopherol is found can be altered to contain predominantly α-tocopherol. Conversely, expression of the antisense RNA would be expected to reduce expression of the γ-tocopherol methyltransferase, causing a decrease in the α-tocopherol: γ-tocopherol ratio. Plants having increased γ-tocopherol may be useful for certain industries.

We have discovered that γ-tocopherol methyltransferase also catalyzes the conversion of δ-tocopherol to β-tocopherol. Overexpression of γ-tocopherol methyltransferase in plant tissue results in increased conversion of δ-tocopherol to β-tocopherol. It is expected that expression of γ-tocopherol methyltransferase antisense RNA would result in reduced conversion of δ-tocopherol to δ-tocopherol.

As demonstrated in the examples below, the seed of Arabidopsis plants transformed with a genetic construct comprising an Arabidopsis γ-tocopherol methyltransferase gene under the control of either the seed specific promoter or the constitutive cauliflower mosaic virus 35S promoter exhibit a dramatic increase in the ratio of α-tocopherol: γ-tocopherol. No α-tocopherol is detected in the seed of untransformed Arabidopsis, whereas seed from Arabidopsis transformed with the γ-tocopherol methyltransferase gene under the control of the seed-specific promoter contained about 90% α-tocopherol. Seed from Arabidopsis transformed with the γ-tocopherol methyltransferase gene under the control of a constitutive promoter contained slightly less α-tocopherol (84%). This observation demonstrates that for plants natively having a tocopherol profile in which α-tocopherol is not predominant (i.e. is less than 50% of total tocopherol), that α-tocopherol can be made to be the predominant tocopherol form in seed or seed oil from a transgenic plant.

Methylation of γ-tocopherol to form α-tocopherol is the means by which the ratio of the di-methylated tocopherols (γ-tocopherol) and tri-methylated tocopherol (α-tocopherol) is regulated. By up regulating γ-tocopherol methyltransferase expression in tissues in which it is not normally expressed in a plant, it is now possible to increase α-tocopherol levels in tissues of many agricultural crops in which γ-tocopherol is a major tocopherol (e.g., maize, soybean, rapeseed, cotton, peanut, safflower, castor bean, rice). Many common edible seed oils have large amounts of γ-tocopherol. Increasing the level of expression of γ-tocopherol methyltransferase in seed oil plants should increase the ratio of α-tocopherol: γ-tocopherol.

Isolation and functional analysis of the γ-tocopherol methyltransferase genes from Synechocystis PCC6803 and *Arabidopsis thaliana* was accomplished by concurrently pursuing the complementary molecular genetic approaches described in detail in the examples. These two model organisms were selected because both synthesize tocopherols by similar or identical pathways and both are highly tractable genetic, molecular, and biochemical systems.

The DNA sequences of the γ-tocopherol methyltransferase genes from Synechocystis PCC6803 and *Arabidopsis thaliana* are shown in SEQ ID NO:1 and SEQ ID NO:3, respectively. The corresponding deduced amino acid sequences of the proteins are shown in SEQ ID NO: 2 and SEQ ID NO:4.

It is expected that the present invention may be practiced using a γ-tocopherol methyltransferase gene from any photosynthetic organism. It is well within the ability of one of skill in the art to isolate a plant γ-tocopherol methyltransferase gene using the sequences disclosed herein. The usefulness of these sequences to identify other γ-tocopherol methyltransferase coding sequences is demonstrated by the fact that it was the Synechocystis sequence that was used to identify the Arabidopsis sequence. The two sequences can be used to screen public computer databases of plant cDNAs (dbest databases) and genomic sequences. Alternatively, the sequences could be used to design probes for use in identifying genomic or cDNA clones containing a γ-tocopherol methyltransferase sequence. Another approach would be to use the sequences to design oligonucleotide primers for use in PCR amplification of γ-tocopherol methyltransferase genes from plant DNA.

To determine whether one has identified a γ-tocopherol methyltransferase sequence, one could perform a gene replacement study using wild type Synechocystis, a complementation study using a Synechocystis γ-TMT knockout mutant, or an in vitro enzyme assay using a suitable substrate and γ-tocopherol methyltransferase protein expressed in *E. coli* or another suitable expression system. A genetic construct comprising the γ-tocopherol methyltransferase coding sequence operably connected to a plant promoter can be constructed and used to transform Arabidopsis or a plant or crop plant of interest. A transgenic plant comprising the construct in its genome would be expected to have altered expression of γ-tocopherol methyltransferase and an altered tocopherol profile relative to an untransformed, wild-type plant.

It is expected that polyploid plants having more than one copy of the γ-tocopherol methyltransferase gene may have allelic variations among γ-tocopherol methyltransferase gene sequences. It is anticipated that putative γ-tocopherol methyltransferase gene sequences having less than 100% homology to SEQ ID NO:1 or SEQ ID NO:3 encode proteins having γ-tocopherol methyltransferase activity.

It is envisioned that minor sequence variations from SEQ NO:1 or SEQ ID NO:3 associated with nucleotide additions, deletions, and mutations, whether naturally occurring or introduced in vitro, will not affect γ-tocopherol methyltransferase activity. The scope of the present invention is intended to encompass minor variations in γ-tocopherol methyltransferase sequences. Also, it is now well within the level of ordinary skill in the art of plant genetic engineering to alter the coding sequence for a gene by changing codons specifying for common amino acids or by making conservative amino acid substitutions at DNA sequences encoding non-critical portions of enzymes.

Construction of an expression vector comprising a γ-tocopherol methyltransferase coding sequence operably connected to a plant promoter not natively associated with the coding sequence will be achieved using standard molecular biology techniques known to the art. The plant promoter may be a tissue-specific promoter such as a seed-specific promoter (e.g., napin or DC3), a constitutive promoter such as CaMV 35S, a developmental stage-specific promoter, or an inducible promoter. Promoters may also contain certain enhancer sequence elements that improve efficiency of transcription. Optionally, the construct may contain a termination signal, such as the nopaline synthase terminator (NOS). Preferably, the constructs will include a selectable or screenable marker to facilitate identification of transformants. The constructs may have the coding region in the sense or antisense orientation.

Once a genetic construct comprising a γ-tocopherol methyltransferase gene has been obtained, it can readily be introduced into a plant or plant tissue using standard methods known to the art. For example, the Agrobacterium transformation system is known to work well with all dicot plants and some monocots. Other methods of transformation equally useful in dicots and monocots may also be used. Transgenic plants may be obtained by particle bombardment, electroporation, or by any other method of transformation known to one skilled in the art of plant molecular biology. The experience to date in the technology of plant genetic engineering has taught that the method of gene introduction does not affect the phenotype achieved in the transgenic plants.

A transgenic plant may be obtained directly by transformation of a plant cell in culture, followed by regeneration of a plant. More practically, transgenic plants may be obtained from transgenic seeds set by parental transgenic plants. Transgenic plants pass on inserted genes, sometimes referred to as transgenes, to their progeny by normal Mendelian inheritance just as they do their native genes. Methods for breeding and regenerating plants of agronomic interest are known to the art. Experience with transgenic plants has also demonstrated that the inserted gene, or transgene, can be readily transferred by conventional plant breeding techniques into any desired genetic background.

It is reasonable to expect that the expression of heterologous γ-tocopherol methyltransferase in a transgenic plant will result in alterations in the tocopherol profile in that plant. In addition to the inherent advantage of increasing the α-tocopherol: γ-tocopherol ratio, changes in the tocopherol profile may result in unique, advantageous phenotypes. This invention is intended to encompass other advantageous phenotypes that may result from alterations in tocopherol biosynthesis in plants obtained by the practice of this invention.

Using the information disclosed in this application and standard methods known to the art, one of skill in the art could practice this invention using any crop plant or forage plant of interest.

The following nonlimiting examples are intended to be purely illustrative.

EXAMPLES

Example 1

Identification and Characterization of a Putative γ-TMT Gene in Synechocystis PCC6803

We recently cloned and characterized the γ-tocopherol methyltransferase gene from Synechocystis as follows. An Arabidopsis p-hydroxyphenyl-pyruvic acid dehydrogenase (HPPDase) cDNA sequence (Norris and Della Penna, submitted, Genbank Accession #AF000228, *Plant Physiol.*, in press) was used to search a database containing the DNA sequence of the Synechocystis PCC6803 genome (Kaneko et al., *DNA Res.* 3:109–136, 1996). We identified an open reading (designated SLR0090) that shares a high degree of amino acid sequence similarity (i.e. 35% identity and 61% similarity) with the Arabidopsis HPPDase enzyme. The putative Synechocystis HPPDase gene is located within an operon in the Synechocystis genome comprised of 10 open reading frames (ORFs) encompassing bases 2,893,184 to 2,905,235 of the published Synechocystis PCC6803 genome (Kaneko et al., supra 1996). We hypothesized that this operon might also contain additional genes that encode other enzymes involved in tocopherol synthesis.

Two ORFs (SLR0089 and SLR0095) were identified as possible candidates for Synechocystis tocopherol methyltransferase genes. BLAST searches with ORFs SLR0089 and SLR0095 showed that these proteins share a high degree of similarity to the known protein sequences of Δ-(24)-sterol-C-methyltransferases and various plant caffeol CoA-O-methyltransferases, respectively. Both SLR0089 and SLR0095 proteins contain consensus sequences corresponding to conserved S-adenosyl-methionine (SAM) binding domains (Kagan and Clarke, *Archives of Biochem. and Biophy.* 310(2):417–427, 1996). The SLR0089 protein contains other structural features that are consistent with features found in a tocopherol methyltransferase. These features were not found in SLR0095. First, PSORT (Prediction of Protein Localization Sites) computer analysis of the two protein sequences predict that SLR0089 is localized to the plasma membrane, whereas and SLR0095 is localized to the cytosol. Tocopherol biosynthesis in cyanobacteria is believed to occur in the plasma membrane; therefore, localization of SLR0089 protein to the plasma membrane suggests that it may be a tocopherol methyltransferase. Additionally, PSORT analysis identified the presence of a putative bacterial signal sequence in the first 25 amino acids of the SLR0089 protein. The predicted molecular weight of the mature SLR0089 protein (after truncation of the signal sequence) is 32,766 daltons, which is very close to the reported molecular weight (33,000 daltons) of purified from pepper fruits (d'Harlingue and Camara, supra 1985). The predicted molecular weight of SLR0095 is 24,322 daltons. Therefore, we concluded that of the two identified ORFs, the SLR0089 gene was more likely to be a tocopherol methyltransferase.

Example 2

Amplification and Cloning of the Synechocystis γ-TMT Gene

Synechocystis genomic DNA was isolated by the method of Williams (*Methods Enzymol.* 167:776–778, 1987). The SLR0089 gene was amplified from Synechocystis genomic DNA by polymerase chain reaction (PCR) using a sense strand specific primer(SLR0089F, SEQ ID NO:5) and a non-sense strand specific primer SLR0089R (SEQ ID NO:6) under the following conditions:

The amplification of the SLR0089 open reading frame was conducted in a 50 μl reaction volume containing 0.4 mM DATP, 0.4 mM dGTP, 0.4 mM dCTP, 0.4 mM dCTP, 0.4 mM dTTP, 0.2 μM SLR0089F primer, 0.2 μM SLR0089R primer, 10 ng Synechocystis PCC6803 genomic DNA, 20 mM Tris-HCl (pH 8.4), 50 mM KCl, 2 mM $MgCl_2$, and 2.5 units Taq polymerase (Gibco-BRL). PCR thermocycle conditions were performed as follows:

5 minutes 95° C. (1 cycle)

1 minute 95° C. →1 minute 55° C. →1.5 minutes 72° C. (35 cycles)

7 minutes 72° C. (1 cycle)

The PCR product comprising the SLR0089 ORF was cloned using standard molecular biological techniques known to one of skill in the art. Briefly, the amplified SLR0089 ORF was purified and made blunt ended by treatment with the Klenow fragment. The SLR0089 gene was ligated to EcoRV-linearized pBluescript KS II (Stratagene, Inc., LaJolla, Calif.). The ligation mixture was used to transform competent *E. coli* DH5α cells, and putative transformants were selected on the basis of ampicillin resistance. A plasmid designated pH-1 that was isolated from a transformant was found to contain the SLR0089 insert. The identity of the SLR0089 gene (SEQ ID NO:1) was confirmed by sequencing using T7 and T3 sequencing primers.

Example 3

Development of a SLR0089 Knockout Mutant

A gene replacement vector was constructed using standard molecular biology techniques. The plasmid pH1, which contains a unique NcoI site in the SLR0089 ORF, was digested with NcoI restriction endonuclease. The aminoglycoside 3'-phospho-transferase gene from Tn903 was ligated to the NcoI site of pH1 and the ligation mixture was used to transform *E. coli* DH5αcells. Transformants were selected using kanamycin and ampicillin. A recombinant plasmid (pQ-1) containing the disrupted SLR0089 ORF was isolated and used to transform Synechocystis PCC6803 according to the method of Williams (*Methods Enzymol.* 167:776–778, 1987).

Synechocystis transformants were selected for on BG-11 medium (Castenholz, *Methods in Enzymology* p 68–93, 1988) containing 15 mM glucose and 15 μg/ml kanamycin. All cultures were grown under continuous light at 26° C. Four independent transformants were carried through five subculturings of single colonies to fresh medium. PCR and genomic analysis were used to confirm that the gene replacement was successful and complete.

Example 4

Tocopherol Profiles of Wild Type and Mutant Synechocystis

Approximately 200 mg of cells were scraped from 2 week old Synechocystis cultures grown on BG-11 agar medium. The cells were homogenized in 6 ml of 2:1 (volume:volume) methanol: $CHCl_3$ containing 1 mg/ml butylated hydroxytolulene (BHT) using a polytron homogenizer. Following homogenization, 2 ml of $CHCl_3$ and 3.4 ml of double-distilled water was added to the homogenate. The lower lipid phase was removed and dried under nitrogen gas. The dried lipids were resuspended in 200 µl of HPLC grade ethyl acetate containing 1 mg/ml BHT.

Tocopherols were analyzed by reverse phase HPLC using a Hewlett-Packard Series 1100 HPLC system with a fluorescence detector. Crude lipid extracts were fractionated on a Water Spherisorb S5 ODS2 4.6×250 mm column in a mobile phase consisting of 75% methanol and 25% isopropanol and a flow rate of 1 ml/min. The fluorescence was measured at 330 nm after excitation at a wavelength of 290 nm.

Wild-type Synechocystis produces α-tocopherol as its most abundant tocopherol (>95% of total tocopherols). The SLR0089 disrupted mutant of Synechocystis is no longer able to synthesize α-tocopherol and instead accumulates γ-tocopherol as its sole tocopherol. The elimination of α-tocopherol production and concomitant accumulation of γ-tocopherol conclusively demonstrates that SLR0089 encodes γ-tocopherol methyltransferase, the final step in α-tocopherol biosynthesis.

Example 5

Identification of a Putative Arabidopsis γ-TMT cDNA from the EST Database

The Arabidopsis EST database (Ausbel et al., *Current Protocols in Molecular Biology*, Greene Publishing and Wiley-Interscience, N.Y., 1987) was searched using the Synechocystis γ-TMT DNA and protein sequences as queries. Two cDNA clones that share significant homology with the Synechocystis sequence were identified: the Arabidopsis Δ(24)-sterol-C-methyltransferase and the Arabidopsis expressed sequence tag (EST) clone 165H5T7. Because the Δ(24)-sterol-C-methyltransferase was functionally identified by its ability to complement a yeast Δ(24)-sterol-C-methyltransferase mutant (erg6), we are confident that the clone does not encode a γ-TMT (Husselstein et al., *FEBS Letters* 381:87–92, 1996). Therefore, we decided to focus our efforts on the Arabidopsis 165H5T7 EST clone (Genbank Accession #R30539). The DNA sequence of the 165H5T7 EST clone was determined (SEQ ID NO:3) and the amino acid sequence of the putative protein was deduced. The sequence was aligned with that of the Synechocystis γ-TMT (FIG. 1). The full-length 165HT7 clone encodes a protein that is 35% identical and 66% similar to the Synechocystis γ-TMT and exhibits large blocks of identity. When 165H5T7 was used as query against the non-repetitive protein database, it was found to have the highest homology to SLR0089 ($P<10_{54}$) and only moderate homology to the four known plant Δ(24)-sterol-C-methyltransferases ($P \geq 10_5$). 165H5T7 also contains conserved SAM binding motifs common to a large number of methyltransferases (FIG. 1) but lacks proposed sterol binding domains common in the four plant Δ(24)-sterol-C-methyltransferases identified to date (Husselstein et al., supra 1990). These data suggest that clone 165H5T7 encodes an Arabidopsis γ-TMT homologue, which we have designated A.t. γ-TMT.

Example 6

Characterization of the Putative Arabidopsis γ-TMT Homologue Using the Gene Replacement in Synechocystis Plant cDNAs encoding putative γ-TMT homologues may be functionally identified using one of two gene replacement approaches in Synechocystis. One approach that may be employed is to replace the endogenous Synechocystis γ-TMT gene in wild type Synechocystis with the putative Arabidopsis γ-TMT cDNA 165H7T7. A Synechocystis γ-TMT(coding sequence #SLR0089) gene replacement vector will be constructed to include the following features, in 5' to 3' order: 1) at least 300 base pairs of DNA sequence corresponding to the Synechocystis genomic sequence found immediately upstream (5') of the native SLR0089 gene; 2) the first 77 base pairs of the SLR0089 ORF corresponding to the identified bacterial signal sequence that ends with a unique, in-frame NcoI site; 3) a polylinker or multiple cloning site; 4) an antibiotic resistance marker (e.g., a kanamycin resistance gene cassette); and 5) at least 300 base pairs of DNA sequence corresponding to the Synechocystis genomic sequence found immediately downstream (3') of the native SLR0089 gene. The putative plant γ-TMT cDNA to be tested for complementation will be inserted into the NcoI site or into the multiple cloning site.

The 165H5T7 cDNA may be engineered to contain an NcoI site at the transit peptide cleavage site predicted by PSORT using PCR mutagenesis, which would change the amino acid Val-48 to Met. The cDNA owill be ligated to the unique NcoI site in the SLR0089 gene replacement plasmid to create an in-frame, amino-terminal fusion between the Synechocystis γ-TMT signal peptide and the plant protein sequence. The construct will be used to transform wild type Synechocystis; transformants will be identified by kanamycin selection. After several single colony passages under selection, gene replacement will be confirmed by PCR. The tocopherol profile of transformants will be determined by HPLC. Synechocystis transformants functionally expressing Arabidopsis γ-TMT genes will be identified by their ability to synthesize α-tocopherol in the absence of a functional Synechocystis γ-TMT gene.

In an alternative approach, the putative γ-TMT gene may be characterized according to its ability to complement the Synechocystis γ-TMT knockout mutant. The replacement vector could be constructed to include the intact putative γ-TMT gene and an antibiotic resistance marker other than kanamycin. Following transformation and selection, gene replacement can be confirmed by PCR and the transformants may be further characterized by tocopherol analysis.

Example 7

Functional Characterization of Arabidopsis and Synechocystis γ-TMT genes by expression in *E. coli*

The proteins encoded by the Synechocystis SLR0089 gene and the Arabidopsis 165h5T7 cDNA clone were identified as γ-TMTs through functional expression in *E. coli*.

The SLR0089 gene was amplified from the Synechocystis PCC6803 genome using polymerase chain reaction (PCR). The forward primer (SLRO089coliF, SEQ ID NO:7), was designed to add a BspHI site to the 5' end of the primer. The reverse (3') PCR primer (SLR0089coliR, SEQ ID NO:8) was designed with a BglII site engineered at the 5' end of the primer.

The PCR reaction was conducted in two 100 -µl reaction mixtures, each of which contained dNTPs (0.4 mM each), 2 µM SLR0089coliF, 2 µM SLR0089coliR, 10 ng Synechocystis PCC6803 genomic DNA, 10 mM KCl, 6.0 mM $(NH_4)_2SO_4$, 20 mM Tris-HCl (pH 8.2), 2 mM $MgCl_2$, 0.1% Triton X-100, 10 µg/ml BSA, 2.5 units Pfu polymerase (Stratagene, LaJolla, Calif.). The following thermocycle conditions were used:

5 minutes 95° C. (1 cycle)
0.75 minutes 94° C. →0.75 minutes 55° C. →2 minutes 72° C. (30 cycles)
10 minutes 72° C. (1 cycle)

The PCR fragment was gel-purified and ligated to EcoRV-linearized pBluescript KS II (Stratagene, LaJolla, Calif.). The ligation product was used to transform E. coli strain DH5α, and putative transformants were selected on the basis of ampicillin resistance. A recombinant plasmid containing the insert (designated p082297) was sequenced to confirm the correct amplification and subcloning of the SLR0089 sequence.

The deduced amino acid sequence of SLR0089 contains a putative amino-terminal bacterial signal sequence comprising the first 24 amino acids of the deduced amino acid sequence. Because this amino-terminal signal sequence could effect the conformation of the SLR0089 protein when expressed in E. coli and render the protein inactive, we modified the SLR0089 DNA sequence such that it encodes a truncated protein devoid of the putative amino-terminal bacterial signal sequence. The SLR0089 gene contains a NcoI recognition sequence at the predicted cleavage site for the putative bacterial signal sequence. A NcoI-BglII fragment containing a truncated SLR0089 DNA sequence from p082297-coli was subcloned in the correct reading frame into the NcoI and BamHI sites of the T7 E. coli pET3D expression vector (Novagen, Madison, Wis.). The ligation mixture was used to transform E. coli BL21 (DE3) and transformants were selected for on the basis of ampicillin resistance. A plasmid (designated p011698-1) containing the insert was identified by restriction digest analysis with the enzyme HindIII.

The 165H5T7 cDNA clone was also subcloned into the pET3D expression vector. The first 50 N-terminal amino acids of the deduced amino acid sequence of 165H5T7 contains a putative amino-terminal chloroplast targeting sequence that could effect the conformation of the 165H5T7 protein when expressed in E. coli and render the protein inactive. Therefore, we modified the 165H5T7 DNA sequence to encode a truncated protein devoid of the putative amino-terminal chloroplast targeting sequence. The truncated 165H5T7 DNA sequence was obtained by PCR amplification of 165H5T7 cDNA using primers designed to amplify the sequence corresponding to the region between nucleotide 353 and nucleotide 1790 of the original 165H5T7 sequence. The forward PCR primer (165matF, SEQ ID NO:9) adds a NcoI site to the 5' end of the truncated 165H5T7 sequence to facilitate cloning into the pET3D vector. The reverse (3') PCR primer (165matR, SEQ ID NO:10) was designed from the polylinker region of the pSPORT1 vector with a AccI site engineered at the 5' end of the primer. The PCR reaction was conducted with the 165matF and 165matR primers (2 µM each) using the same PCR conditions described for the amplification of the truncated Synechocystis gene, above.

Following gel purification, the PCR fragment was ligated to EcoRV-linearized pBluescript KS II, the ligation product was used to transform E. coli strain DH5α, and ampicillin-resistant putative transformants were selected. A recombinant plasmid (designated p010498-2) containing the insert was identified. The DNA sequence of p010498-2 was determined to confirm the correct amplification and subcloning of the truncated 165H5T7 sequence. The truncated 165H5T7 DNA sequence was subcloned as a NcoI-BamHI fragment pET3D vector digested with NcoI and BamHI. The ligation product was used to transformed E. coli DH5α and transformants were selected for on the basis of ampicillin resistance. A plasmid (designated p011898-1) containing the insert was identified by restriction digest analysis with the enzyme HindIII.

The p011698-1 and p011898-1 constructs were used to transform the E. coli T7 expression host BL21(DE3). To generate protein for γ-TMT assays, one liter cultures of transformed host cells containing one of the constructs were grown in Luria broth containing 100 mg/liter ampicillin. Each culture was started at an optical density at 600 nm ($OD_{600}$) of 0.1 and incubated in a shaking incubator at 28° C. until the culture reached an $OD_{600}$ of 0.6, at which time isopropyl-, β-D-thiogalactopyranoside (IPTG) was added to each culture to obtain a final concentration of 0.4 mM IPTG. Each culture was incubated for an additional 3 hours at 28° C. and the cells were harvested by centrifugation at 8,000 g. The cell pellets were then resuspended in 10 ml of 10 mM HEPES (pH 7.8), 5 mM DTT, 0.24 M sorbitol, 1 mM PMSF. The cells were lysed by sonication with a micro-tip sonicator using four 10-second pulses. Triton×100 was added to each homogenate to a final concentration of 1%. The homogenates were incubated on ice for 30 minutes, and subjected to centrifugation at 30,000 g for 30 minutes at 4° C. The supernatants of these extracts were assayed for γ-tocopherol methyltransferase activity as follows.

The γ-TMT assays were performed in 250 µl volumes containing 50 mM Tris (pH 7.5 for the Synechocystis and pH 8.5 for the Arabidopsis enzyme), 5 mM DTT, 5 mM γ- or δ-tocopherol, and 0.025 µCi (55 µCi/mmole) ($^{14}$C-methyl)-S-adenosylmethionine. Reaction mixtures were incubated at room temperature for 30 minutes. The reactions were stopped by adding of 1 ml of 2:1 (v:v) $CHCl_3$: methanol containing 1 mg/ml butylated hydroxytoluene (BHT) and 250 µl of 0.9% NaCl in water, and vortexing. The samples were centrifuged to separate the phases. The $CHCl_3$ (lower) phase was transferred to a fresh tube containing 100 mg of α-tocopherol and the $CHCl_3$ was then removed under vacuum in a speed-vac. The dried lipid fraction was resuspended in 50 µl ethyl acetate containing 1 mg/ml BHT. The lipid extracts were fractionated on silica 60 TLC plates in dichloromethane. Tocopherols were then identified by co-migration with authentic tocopherol standards after staining the plate with Emmerie-Engels solution (0.1% FeCl3, 0.25% 2,2'-dipyridyl in ethanol). The band corresponding to α-tocopherol was scraped from the TLC plate and the amount of radioactive material present was determined by scintillation counting. These experiments showed that the proteins encoded by the Synechocystis SLR0089 and Arabidopsis 165H5T7 DNA sequences were able to convert γ-tocopherol to α-tocopherol.

The Synechocystis and Arabidopsis γ-tocopherol methyltransferases were tested for activity using several different methyl-substituted tocopherol substrates. Both enzymes were able to specifically convert δ-tocopherol to β-tocopherol. The two enzymes were unable to use tocol, 5,7-diemethyltocol, β-tocopherol, and γ-tocotrienol as substrates. These results indicate that both the Synechocystis and Arabidopsis γ-tocopherol methyltransferases catalyze the methylation of carbon 5 of the tocopherol chromanol ring. The Synechocystis and Arabidopsis γ-TMTs appear to require substrates with a methyl-group present on the 8 position of the chromanol ring and a fully saturated prenyl-tail for activity. Our results indicate that Arabidopsis γ-TMT exhibits greater activity with γ-tocopherol as the substrate than with the δ-tocopherol substrate, whereas the Synechocystis γ-TMT appears to be equally active toward γ-tocopherol and δ-tocopherol.

Example 8

Qualitative Manipulation of Tocopherols in Arabidopsis and Other Plants by Over Expressing the Arabidopsis γ-Tocopherol Methyltransferase The results from HPLC analysis of lipid extracts made from Arabidopsis leaves and seeds indicate that these tissues have relatively simple tocopherol profiles. In Arabidopsis leaves, α-tocopherol is present at 90% of the total tocopherol content, with γ-tocopherol comprising the remainder of the tocopherol content. In Arabidopsis seeds, γ-tocopherol is present at 95% of the total tocopherol content in Arabidopsis seeds with the remaining 5% being composed of δ-tocopherol. These simple tocopherol profiles make Arabidopsis seed and leaf tissue ideal targets for evaluating the functional consequences of altering the expression of a γ-tocopherol methyltransferase gene in plants.

We hypothesized that increasing the expression of a γ-tocopherol methyltransferase gene in Arabidopsis would increase α-tocopherol levels as a proportion of the total tocopherols. To test this hypothesis, the full-length Arabidopsis γ-tocopherol methyltransferase cDNA clone 165H5T7 was over-expressed under the control of the strong constitutive cauliflower mosaic virus 35S transcript (CaMV 35S) promoter and the embryo-specific carrot DC3 promoter (Seffens W S et al., *Dev. Genet.* 11: 65–76, 1990) in transgenic Arabidopsis.

The seed-specific plant gene expression plasmid was constructed from a derivative of the Agrobacterium plant transformation vector, pBIB-Hyg (Becker, D. *Nucleic Acids Res.* 18:203, 1990). The carrot embryo DC3 promoter was isolated from the plasmid pBS-DC3 5' PH after digestion with HindIII and BamHI. The DC3 HindIII and BamHI promoter fragment was then treated with DNA polymerase to fill in the 5' over-hanging ends. The pBIB-Hyg plasmid was digested with HindIII and then treated with DNA polymerase to fill-in the 5' over-hanging ends. The DC3 promoter fragment was ligated to pBIB-Hyg to create a plasmid designated p111397. The Arabidopsis γ-tocopherol methyltransferase cDNA 165H5T7 was subcloned in the sense orientation as a SalI-XbaI fragment into the SalI and XbaI sites of p111397 to obtain p122997. The p122997 plasmid has the following features: 1) plant hygromycin selectable marker; 2) Agrobacterium T-DNA left and right border sequences; 3) the Arabidopsis 165H5T7 γ-tocopherol methyltransferase cDNA cloned between the carrot seed specific DC3 promoter and the nopoline synthase 3' transcriptional termination sequences; 4) the RK2 broad host bacterial plasmid origin of replication; and 5) bacterial kanamycin resistance selectable marker.

The constitutive Arabidopsis γ-tocopherol methyltransferase gene expression plasmid was derived from pSN506 CaMV 35S binary plant expression vector, a pART27 derivative in which the p-hydroxyphenol pyruvic acid dioxygenase (HPPDase) cDNA is under the control of the CaMV 35S promoter. (Norris and Della Penna, in press). The CaMV 35S/γ-tocopherol methyltransferase construct was made by replacing the HPPDase cDNA with the full length 165H5T7 cDNA sequence. The HPPDase cDNA fragment was removed from pSN506 by digesting the plasmid with XbaI and XhoI. The 5' DNA over-hanging ends of the pSN506 XbaI-XhoI vector fragment were filled in using the Klenow fragment of the *E. coli* DNA polymerase. The linearized vector was ligated to a blunt-ended XbaI-SalI fragment from 165H5T7 encoding the full length γ-tocopherol methyltransferase. A recombinant plasmid containing the insert was obtained and designated p010398. The plasmid p010398 contains the following characteristics: 1) plant kanamycin selectable marker; 2) agrobacterium T-DNA left and right border sequences; 3) the Arabidopsis 165H5T7 γ-tocopherol methyltransferase cDNA cloned between the CaMV 35S promoter and the nopoline synthase 3' transcriptional termination sequences; 4) the RK2 broad host bacterial plasmid origin of replication; and 5) bacterial kanamycin resistance selectable marker.

The constitutive and seed specific γ-tocopherol methyltransferase plant gene expression constructs (p122997 and p010398) and the appropriate empty vector control vectors (pART27 and p111397) were used to transform *Agrobacterium tumefaciens* strain C58 GV3101. Wild type Arabidopsis (ecotype Columbia) plants were transformed with these Agrobacterium strains using the vacuum infiltration method (Bechtold N, Ellis J, Pelletier G, in planta Agrobacterium mediated gene transfer by infiltration of adult Arabidopsis thaliana plants. CR Acad Sci Paris, 1993. 1144(2): 204–212). Seeds from the primary transformants were selected for resistance to the appropriate antibiotic on medium containing MS salts, 1% sucrose, 0.7% agar, and suitable levels of the antibiotic. Antibiotic resistant seedlings (representing the T1 generation) were transferred to soil and grown to maturity. Leaf and seed material from these T1 generation plants were analyzed by HPLC.

Example 9

Characterization of Transgenic Plants

A. Analysis of Transgenic Arabidopsis Tocopherol Profiles

Known weights of approximately 5 mg of plant material (i.e. seed or leaf) and 100 ng of tocol (for use as an internal standard) were homogenized in 300 μl of 2:1 (V/V) methanol: $CHCl_3$ containing 1 mg/ml butylated hydroxytolulene (BHT). One hundred μl of $CHCl_3$ and 180 μl of 0.9% (w/v) NaCl in water were added to the homogenate and the mixture was briefly vortexed. The mixture was then centrifuged and the lower ($CHCl_3$) fraction was removed and transferred to a fresh tube. The $CHCl_3$ fraction was dried under vacuum and the resulting lipid residue was resuspended in 100 μl of ethyl acetate for analysis by C18 reverse phase HPLC or in 100 μl of hexane for analysis by normal phase HPLC.

Crude lipid extracts were analyzed by normal phase or reverse phase HPLC for changes in tocoperhol profiles. Individual tocopherol species were quantified by comparing their fluorescence signals with standard curves made from known quantities of authentic tocopherol standards. Reverse phase HPLC was done as describe in example 4. Normal phase HPLC analysis was done on a Licosorb Si60A 4.6× 250 mm HPLC column using the following conditions:

Column temperature: 42° C.
mobile phase: solvent A=HPLC grade hexane
solvent B=diisopropylether

| Gradient: (ml/min) | time | % solvent A | % solvent B | flow rate |
|---|---|---|---|---|
| | 0 | 92% | 8% | 1 |
| | 20 | 82% | 18% | 1 |
| | 25 | 82% | 18% | 1 |
| | 25 | 92% | 8% | 2 |
| | 34 | 92% | 8% | 2 |

Fluorescence Detector Settings:
excitation wavelength: 290 nm
emmission wavelentgh: 325nm The concentrations of the various tocopherol species obtained by HPLC analysis of T1 seed material from Arabidopsis plants transformed with p122997, p010398, p111398, pART27 are shown in Table 1. Plants overexpressing the γ-tocopherol methyltransferase using either the CaMV 35S or carrot DC3 promoters are able to convert the majority of the γ-tocopherol normally present in Arabidopsis seeds to α-tocopherol and also are able to convert the majority of the δ-tocopherol normally present in Arabidopsis seeds to β-tocopherol. These results show that γ-tocopherol methyltransferase activity is normally limiting in Arabidopsis seeds.

B. Analysis of γ-Tocopherol Methyltransferase Activity in Transgenic Arabidopsis Seed Seeds from the Ti generation plants transformed with p122997, p010398, p111397, and pART27 were assayed for γ-tocopherol methyltransferase activity. Protein extracts were made by homogenizing approximately 10 mg of seeds in 200 μl of 50 mM Tris pH 8.5, 5 mM DTT, 1% Triton×100, 1 mM PMSF. The extracts were centrifuged for 5 minutes to remove insoluble material. A 25 -μl aliquot of each extract supernatant was assayed for γ-tocopherol methyltransferase activity as described in example 7. No γ-tocopherol methyltransferase activity was detected in wild type seeds and empty vector controls. Activity in seed-specific lines was approximately 2 pmol/hr/mg protein, and in 35S constitutive expression lines activity was 0.5 pmol/hr/mg protein.

Example 11

Other Transgenic Plants

Based on this data demonstrating that a simple insert of a α-tocopherol methyl transferase gene into a plant can dramatically change the relative proportions of tocopherols in a plant seed, it becomes possible to reasonably suggest the similar results that can be obtained in other plant species.

It is expected that one may manipulate tocopherol profiles in any plant species using the methods disclosed in the examples. Based on the concentration of the various tocopherols in untransformed plant tissue, we have predicted tocopherol profiles obtainable for a variety of plant tissue (Table 2). Note that several common plant oils (e.g. soybean) which are predominantly γ-tocopherol and contain low levels of α-tocopherol can be altered to be predominantly α-tocopherol.

All publications cited in this patent application are incorporated by reference herein.

The present invention is not limited to the exemplified embodiment, but is intended to encompass all such modifications and variations as come within the scope of the following claims.

TABLE 1

| | ng α-tocopherol/ mg seed (% total tocopherol) | ng β-tocopherol/ mg seed (% total tocopherol) | ng γ-tocopherol/ mg seed (% total tocopherol) | ng δ-tocopherol/ mg seed (% total tocopherol) | ng total-tocopherol/mg seed (% total tocopherol) |
|---|---|---|---|---|---|
| 122997-1 (seed specific promoter/ Arabidopsis γ-TMT) | 523.28 ± 45.06 (88.91%) | 23.91 ± 3.81 (4.06%) | 41.38 ± 4.05 (7.03%) | ND (0%) | 588.55 ± 48.02 (100%) |
| 111397-2 (seed specific promoter/ empty vector control) | ND (0%) | ND (0%) | 409.16 ± 6.82 (95.11%) | 17.81 ± 0.82 (4.89%) | 430.19 ± 7.05 (100%) |
| 010398-1 (constitutive promoter/ Arabidopsis γ-TMT) | 373.85 ± 15.25 (83.74%) | 17.16 ± 0.87 (3.84%) | 55.41 ± 5.12 (12.41%) | ND (0%) | 446.43 ± 18.46 (100%) |
| ART27-1 (constitutive promoter/ empty vector control) | ND (0%) | ND (0%) | 409.99 ± 7.00 (96.41%) | 15.41 ± 0.11 (3.62%) | 425.28 ± 6.80 (88.91%) |

ND = none detected
All samples were analyzed in triplicate

TABLE 2

| Crop Species (tissue) | Tocopherol composition of untransformed plant | Expected tocopherol composition of transgenic plants with γ-TMT over-expressed |
|---|---|---|
| Soybean[1] (seed/oil) | 70% γ-tocopherol<br>22% δ-tocopherol<br>7% α-tocopherol<br>1% β-tocopherol | 77% α-tocopherol<br>23% β-tocopherol |
| Oil Palm[1] (seed/oil) | 25% α-tocopherol<br>30% α-tocotrienol<br>40% γ-tocotrienol<br>5% δ-tocotrienol | 25% α-tocopherol<br>70% α-tocotrienol<br>5% β-tocotrienol |
| Peanut[2] (raw nut) | 50% α-tocopherol<br>50% γ-tocopherol | 100% α-tocopherol |
| Peanut[2] (nut oil) | 33% α-tocopherol<br>66% γ-tocopherol | 100% α-tocopherol |
| Safflower[2] (seed oil) | 48% α-tocopherol<br>22% γ-tocopherol<br>30% δ-tocopherol | 70% α-tocopherol<br>30% β-tocopherol |
| Rapeseed[2] (seed oil) | 25% α-tocopherol<br>75% δ-tocopherol | 100% α-tocopherol |
| Cotton Seed[1] (seed oil) | 40% α-tocopherol<br>58% γ-tocopherol<br>2% δ-tocopherol | 98% α-tocopherol<br>2% β-tocopherol |
| Wheat[2] (whole wheat flour) | 20% α-tocopherol<br>7% α-tocotrienol<br>17% β-tocopherol<br>56% β-tocotrienol | 20% α-tocopherol<br>7% α-tocotrienol<br>17% β-tocopherol<br>56% β-tocotrienol |
| Wheat[1] (germ oil) | 75% α-tocopherol<br>25% γ-tocopherol | 100% α-tocopherol |

TABLE 2-continued

| Crop Species (tissue) | Tocopherol composition of untransformed plant | Expected tocopherol composition of transgenic plants with γ-TMT over-expressed |
|---|---|---|
| Corn[1] (oil) | 22% α-tocopherol | 90% α-tocopherol |
| | 68% γ-tocopherol | 10% β-tocopherol |
| | 3% β-tocopherol | |
| | 7% β-tocopherol | |
| Castor Bean[2] (oil) | 50% γ-tocopherol | 50% α-tocopherol |
| | 50% δ-tocopherol | 50% β-tocopherol |
| Corn[2] (whole grain) | 11% α-tocopherol | 80% α-tocopherol |
| | 69% γ-tocopherol | 13% α-tocotrienol |
| | 4% α-tocotrienol | 7% β-tocotrienol |
| | 9% γ-tocotrienol | |
| | 7% γ-tocotrienol | |
| Barley[2] (whole grain) | 14% α-tocopherol | 16% α-tocopherol |
| | 2% γ-tocopherol | 10% β-tocopherol |
| | 10% β-tocopherol | 51% α-tocotrienol |
| | 44% α-tocotrienol | 23% β-tocotrienol |
| | 7% γ-tocotrienol | |
| | 23% β-tocotrienol | |
| Rice[2] (whole grain) | 50% α-tocopherol | 100% α-tocopherol |
| | 50% γ-tocopherol | |
| Potato[2] (tuber) | 95% α-tocopherol | 100% α-tocopherol |
| | 5% γ-tocopherol | |
| Sunflower[2] (seeds raw) | 95% α-tocopherol | 100% α-tocopherol |
| | 5% γ-tocopherol | |
| Sunflower[1] (seed oil) | 96% α-tocopherol | 98% α-tocopherol |
| | 2% γ-tocopherol | 2% β-tocopherol |
| | 2% β-tocopherol | |
| Banana[1] (fruit) | 100% α-tocopherol | 100% α-tocopherol |
| Lettuce[1] (leaf) | 53% α-tocopherol | 100% α-tocopherol |
| | 47% γ-tocopherol | |
| Broccoli[2] | 72% α-tocopherol | 100% α-tocopherol |
| | 28% γ-tocopherol | |
| Cauliflower[2] | 44% α-tocopherol | 100% α-tocopherol |
| | 66% γ-tocopherol | |
| Cabbage[1] | 100% α-tocopherol | 100% α-tocopherol |
| Apple[2] | 100% α-tocopherol | 100% α-tocopherol |
| Pears[2] | 93% α-tocopherol | 100% α-tocopherol |
| | 7% γ-tocopherol | |
| Carrots[2] | 94% α-tocopherol | 98% α-tocopherol |
| | 4% γ-tocopherol | 2% β-tocopherol |
| | 2% δ-tocopherol | |

[1]McLaughlin, P. J, Weihrauch, J. C. "Vitamin E content of foods", J. Am. Diet Ass. 75: 647–665 (1979).
[2]Bauernfeind, J. "Tocopherols in foods", In Vitamin E: A Comprehensive Treatise, L. J Machlin ed., Marcel Dekker, Inc. New York pp 99–168.

---

We claim:

1. An isolated DNA sequence consisting of SEQ ID NO:3.

2. An isolated DNA construct comprising an Arabidopsis γ-tocopherol methyltransferase coding sequence operably connected to a plant promoter not natively associated with the coding sequence.

3. A genetic construct comprising a γ-tocopherol methyltransferase coding sequence operably connected to a plant promoter not natively associated with the coding sequence, wherein the γ-tocopherol methyltransferase coding sequence is selected from the group consisting of SEQ ID NO:1 and SEQ ID NO:3.

4. A transgenic plant comprising in its genome the genetic construct of claim 3.

5. The plant of claim 4, wherein the plant has an altered α-tocopherol:γ-tocopherol ratio relative to an untransformed wild-type plant.

6. The seed of the plant of claim 5.

7. The plant of claim 4, wherein the plant has an altered δ-tocopherol:β-tocopherol ratio relative to an untransformed wild-type plant.

8. The seed of the plant of claim 7.

9. A transgenic plant having an altered relative proportion of tocopherols in its tissues as compared to non-transgenic plants of the same species, the transgenic plant comprising in its genome an inserted γ-tocopherol methyltransferase coding sequence, the γ-tocopherol methyltransferase coding sequence selected from the group consisting of SEQ ID NO:1 and SEQ ID NO:3.

10. The plant of claim 9 wherein the γ-tocopherol methyltransferase is in the sense orientation.

11. The plant of claim 9 wherein the γ-tocopherol methyltransferase is in its antisense orientation.

12. A method of producing α-tocopherol comprising the steps of:
(a) constructing an expression host cell comprising in its genome a γ-tocopherol methyltransferase coding sequence operably connected to a promoter not natively associated with the sequence, wherein the promoter is functional in the host cell, the γ-tocopherol methyltransferase gene encoding proteins selected from the group consisting of SEQ ID NO:2 and SEQ ID NO:4;
(b) culturing the host cell under conditions suitable to allow expression of the γ-tocopherol methyltransferase; and
(c) reacting γ-tocopherol and S-adenosylmethionine with the γ-tocopherol methyltransferase protein of step b under suitable conditions and for a period of time sufficient to allow conversion of γ-tocopherol to α-tocopherol.

* * * * *